United States Patent
Peters et al.

(10) Patent No.: US 7,358,243 B2
(45) Date of Patent: Apr. 15, 2008

(54) DIAZABICYCLONANE AND-DECANE DERIVATIVES AND THEIR USE AS OPIOID RECEPTOR LIGANDS

(75) Inventors: Dan Peters, Malmoe (SE); Gunnar M. Olsen, Smoerum (DK); Elsebet Østegaard Nielsen, Koebenhavn K (DK)

(73) Assignee: Neurosearch A/S, Ballerup (DK)

( * ) Notice: Subject to any disclaimer, the term of this patent is extended or adjusted under 35 U.S.C. 154(b) by 328 days.

(21) Appl. No.: 10/521,559

(22) PCT Filed: Jul. 24, 2003

(86) PCT No.: PCT/DK03/00510

§ 371 (c)(1),
(2), (4) Date: Jan. 19, 2005

(87) PCT Pub. No.: WO2004/011468

PCT Pub. Date: Feb. 5, 2004

(65) Prior Publication Data

US 2005/0239773 A1      Oct. 27, 2005

(30) Foreign Application Priority Data

Jul. 26, 2002  (DK) .............................. 2002 01143

(51) Int. Cl.
*A61P 21/02*    (2006.01)
*A61K 31/551*   (2006.01)
*C07D 487/08*   (2006.01)

(52) U.S. Cl. ...................................... 514/221; 540/556
(58) Field of Classification Search ................ 514/221; 540/556

See application file for complete search history.

(56) References Cited

U.S. PATENT DOCUMENTS 5,672,601 A    9/1997   Cignarella .................. 514/249

FOREIGN PATENT DOCUMENTS

| WO | WO-00/66586 A1 | 11/2000 |
| WO | WO-01/60823 A1 | 8/2001 |
| WO | WO-01/72303 A1 | 10/2001 |

OTHER PUBLICATIONS

Razdan et al., "Studies on azabicyclo systems: synthesis and spasmolytic activity of analogues of 9-methyl-3,9-diazabicyclo[4.2.1]nonane and 10-methyl-3, 10-diazabicyclo[4.3.1]decane", Eur. J. Med. Chem., vol. 22, 1987, pp. 573-577.

*Primary Examiner*—Brenda L Coleman
(74) *Attorney, Agent, or Firm*—Birch, Stewart, Kolasch & Birch, LLP

(57) ABSTRACT

This invention relates to novel diazabicyclononane and -decane derivatives useful as opioid receptor ligands. More specifically, the invention provides compounds useful as μ opioid receptor ligands.

10 Claims, No Drawings

DIAZABICYCLONANE AND -DECANE DERIVATIVES AND THEIR USE AS OPIOID RECEPTOR LIGANDS

This application is a national stage entry under 35 U.S.C. § 371 PCT/DK03/00510, filed Jul. 24, 2003.

TECHNICAL FIELD

This invention relates to novel diazabicyclononane and -decane derivatives useful as opioid receptor ligands. More specifically, the invention provides compounds useful as μ opioid receptor ligands.

In other aspects the invention relates to the use of these compounds in a method for therapy, such as for the treatment of pain, and to pharmaceutical compositions comprising the compounds of the invention.

BACKGROUND ART

Numerous classes of opioid receptors exist. These classes differ in their affinity for various opioid ligands and in their cellular and organ distribution. Moreover, although the different classes are believed to serve different physiological functions, there is a substantial overlap of function, as well as distribution. Three different types of opioid receptors have been identified, the mu (μ), delta (δ) and kappa (κ) opioid receptor. These three opioid receptor types are the sites of action of opioid ligands producing analgesic effects. However, the type of pain inhibited and the secondary functions vary with each receptor type. The μ receptor is generally regarded as primarily associated with pain relief, and drug or other chemical dependence, such as addiction or alcoholism. The δ receptor appears to deal with behavioural effects, although the δ and the κ receptors may also mediate analgesia.

Each opioid receptor, when coupled with an opiate, causes a specific biological response unique to that type of receptor. When an opiate activates more than one receptor, the biological response for each receptor is affected, thereby producing side effects. The less specific and selective an opiate may be, the greater the chance of causing increased side effect by the administration of the opiate.

Whereas morphine, which is a strong opioid analgetic agent shows effectiveness against strong pain by acting on the μ opioid receptor (agonist activity), there is a problem that its side effects such as nausea and neurologic manifestation including hallucination and derangement. Moreover, morphine forms psychological dependence, causing serious problems. Other side effects reported are respiratory depression, tolerance, physical dependence capacity, and precipitated withdrawal syndrome, caused by non-specific interactions with central nervous receptors.

WO 01/60823 describes 3,9-diazabicyclo[3.3.1]nonane derivatives with analgesic activity.

WO 01/72303 describes selective ligands for the δ opioid receptor.

SUMMARY OF THE INVENTION

It is an object of the invention to provide novel compounds which act on opiate receptors.

A further object of the invention is the provision of compounds that substantially avoid the unwanted side effects associated with conventional peripherally acting analgesics.

It is a further object to provide compounds that bind selectively to the μ opioid receptor.

In its first aspect, the invention provides a compound of general formula I,

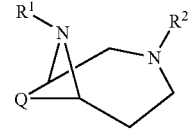

(I)

any of its enantiomers or any mixture of its enantiomers, or a pharmaceutically acceptable salt thereof, wherein Q, $R^1$, and $R^2$ are as defined below.

In its second aspect, the invention provides a pharmaceutical composition, comprising a therapeutically effective amount of a compound of the invention, or any of its enantiomers or any mixture of its enantiomers, or a pharmaceutically acceptable salt thereof, together with at least one pharmaceutically acceptable carrier, excipient or diluent.

In a further aspect, the invention provides the use of a compound of the invention, or any of its enantiomers or any mixture of its enantiomers, or a pharmaceutically acceptable salt thereof, for the manufacture of a pharmaceutical composition for the treatment, prevention or alleviation of a disease or a disorder or a condition of a mammal, including a human, which disease, disorder or condition is responsive to modulation of the opioid receptor.

In a still further aspect, the invention relates to a method for treatment, prevention or alleviation of a disease or a disorder or a condition of a living animal body, including a human, which disorder, disease or condition is responsive to responsive to modulation of the opioid receptor, which method comprises the step of administering to such a living animal body in need thereof a therapeutically effective amount of a compound of the invention, or any of its enantiomers or any mixture of its enantiomers, or a pharmaceutically acceptable salt thereof.

Other objects of the invention will be apparent to the person skilled in the art from the following detailed description and examples.

DETAILED DISCLOSURE OF THE INVENTION

Diazabicyclononane and -decane derivatives

In its first aspect, the invention provides a compound of general formula I,

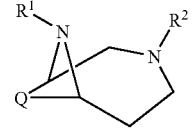

(I)

any of its enantiomers or any mixture of its enantiomers, or a pharmaceutically acceptable salt thereof, wherein
Q is —$CH_2$—$CH_2$— or —$CH_2$—$CH_2$—$CH_2$—;
one of $R^1$ and $R^2$ is —$CH_2$—$CH_2$—$CH_2$—$R^3$, —$CH_2$—CH=CH—$R^3$, or —$CH_2$—C≡C—$R^3$;
  wherein $R^3$ is aryl or heteroaryl;
  which aryl and heteroaryl is optionally substituted with one or more substituents selected from the group consisting of:
  halogen, hydroxy, amino, cyano, nitro, trifluoromethyl, alkoxy, cycloalkoxy, alkyl, cycloalkyl, cycloalkylalkyl, alkenyl, and alkynyl; and the other of $R^1$ and $R^2$ is —CO—$R^4$;

wherein $R^4$ is alkyl, cycloalkyl, cycloalkylalkyl, aryl, or arylalkyl.

In one embodiment of the compound of general formula I, Q is —$CH_2$—$CH_2$—.

In a second embodiment of the compound of general formula I, Q is —$CH_2CH_2$—$CH_2$—.

In a third embodiment of the compound of general formula I, one of $R^1$ and $R^2$ is —$CH_2$—CH=CH—$R^3$; wherein $R^3$ is defined as above. In a further embodiment, one of $R^1$ and $R^2$ is —$CH_2$—$CH_2$—$CH_2$—$R^3$; wherein $R^3$ is defined as above. In a still further embodiment, one of $R^1$ and $R^2$ is —$CH_2$—C≡C—$R^3$; wherein $R^3$ is defined as above.

In a further embodiment of the compound of general formula I, $R^3$ is optionally substituted aryl, such as optionally substituted phenyl. In a special embodiment, $R^3$ is phenyl.

In s special embodiment of the compound of general formula I, one of $R^1$ and $R^2$ is —$CH_2$—CH=CH—$R^3$; wherein $R^3$ is phenyl.

In a still further embodiment of the compound of general formula I, $R^4$ is alkyl. In a further embodiment, $R^4$ is aryl, such as phenyl. In a special embodiment, $R^4$ is methyl or ethyl.

In a further embodiment of the compound of general formula I,
Q is —$CH_2$—$CH_2$— or —$CH_2$—$CH_2$—$CH_2$—;
one of $R^1$ and $R^2$ is —$CH_2$—CH=CH—$R^3$, or —$CH_2$—C≡C—$R^3$;
wherein $R^3$ is phenyl; and
the other of $R^1$ and $R^2$ is —CO—$R^4$; wherein $R^4$ is alkyl.

In a still further embodiment, $R^1$ is —$CH_2$—CH=CH—$R^3$, or —$CH_2$—C≡C—$R^3$; wherein $R^3$ is phenyl; and $R^2$ is —CO—$R^4$; wherein $R^4$ is alkyl.

In a further embodiment, $R^1$ is —CO—$R^4$; wherein $R^4$ is alkyl and $R^2$ is —$CH_2$—CH=CH—$R^3$, or —$CH_2$—C≡C—$R^3$; wherein $R^3$ is phenyl.

In a special embodiment the compound of the invention is
(±)-1-[9-(3-Phenyl-allyl)-3,9-diaza-bicyclo[4.2.1]non-3-yl]-propan-1-one;
(±)-1-[10-(3-Phenyl-allyl)-3,10-diaza-bicyclo[4.3.1]dec-3-yl]-propan-1-one;
(±)-1-[3-(3-Phenyl-allyl-3,9-diazabicyclo[4.2.1]non-9-yl]-propan-1-one;

or any of its enantiomers or any mixture of its enantiomers, or a pharmaceutically acceptable salt thereof.

Any combination of two or more of the embodiments described herein is considered within the scope of the present invention.

Definition of Substituents

In the context of this invention halogen represents a fluorine, a chlorine, a bromine or an iodine atom.

Alkyl means a straight chain or branched chain of one to six carbon atoms, including but not limited to, methyl, ethyl, propyl, isopropyl, butyl, isobutyl, t-butyl, pentyl, and hexyl; methyl, ethyl, propyl and isopropyl are preferred groups.

Cycloalkyl means cyclic alkyl of three to seven carbon atoms, including but not limited to cyclopropyl, cyclobutyl, cyclopentyl, and cyclohexyl;

Alkenyl means a group of from two to six carbon atoms, including at least one double bond, for example, but not limited to ethenyl, 1,2- or 2,3-propenyl, or 1,2-, 2,3-, or 3,4-butenyl.

Alkynyl means a group of from two to six carbon atoms, including at least one triple bond, for example, but not limited to ethynyl, 1,2-, 2,3-propynyl, or 1,2-, 2,3- or 3,4-butynyl.

Alkoxy is O-alkyl, wherein alkyl is as defined above.

Cycloalkoxy means O-cycloalkyl, wherein cycloalkyl is as defined above.

Cycloalkylalkyl means cycloalkyl as above and alkyl as above, meaning for example, cyclopropylmethyl.

Amino is $NH_2$ or NH-alkyl or N-(alkyl)$_2$, wherein alkyl is as defined above.

Aryl is a carbocyclic aromatic ring system such as phenyl or naphthyl (1-naphthyl or 2-naphthyl).

Heteroaryl is a 5- or 6-membered heterocyclic monocyclic group, for example, but not limited to, oxazol-2-yl, oxazol-4-yl, oxazol-5-yl, isoxazol-3-yl, isoxazol-4-yl, isoxazol-5-yl, thiazol-2-yl, thiazol-4-yl, thiazol-5-yl, isothiazol-3-yl, isothiazol-4-yl, isothiazol-5-yl, 1,2,4-oxadiazol-3-yl, 1,2,4-oxadiazol-5-yl, 1,2,4-thiadiazol-3-yl, 1,2,4-thiadiazol-5-yl, 1,2,5-oxadiazol-3-yl, 1,2,5-oxadiazol-4-yl, 1,2,5-thiadiazol-3-yl, 1,2,5-thiadiazol4-yl, 2-imidazolyl, 4-imidazolyl, 5-imidazolyl, 2-pyrrolyl, 3-pyrrolyl, 2-furanyl, 3-furanyl, 2-thienyl, 3-thienyl, 2-pyridyl, 3-pyridyl, 4-pyridyl, 2-pyrimidyl, 4-pyrimidyl, 5-pyrimidyl or 6-pyrimidyl.

Pharmaceutically Acceptable Salts

The chemical compound of the invention may be provided in any form suitable for the intended administration. Suitable forms include pharmaceutically (i.e. physiologically) acceptable salts, and pre- or prodrug forms of the chemical compound of the invention.

Examples of pharmaceutically acceptable addition salts include, without limitation, the non-toxic inorganic and organic acid addition salts such as the hydrochloride derived from hydrochloric acid, the hydrobromide derived from hydrobromic acid, the nitrate derived from nitric acid, the perchlorate derived from perchloric acid, the phosphate derived from phosphoric acid, the sulphate derived from sulphuric acid, the formate derived from formic acid, the acetate derived from acetic acid, the aconate derived from aconitic acid, the ascorbate derived from ascorbic acid, the benzene-sulphonate derived from benzensulphonic acid, the benzoate derived from benzoic acid, the cinnamate derived from cinnamic acid, the citrate derived from citric acid, the embonate derived from embonic acid, the enantate derived from enanthic acid, the fumarate derived from fumaric acid, the glutamate derived from glutamic acid, the glycolate derived from glycolic acid, the lactate derived from lactic acid, the maleate derived from maleic acid, the malonate derived from malonic acid, the mandelate derived from mandelic acid, the methanesulphonate derived from methane sulphonic acid, the naphthalene-2-sulphonate derived from naphtalene-2-sulphonic acid, the phthalate derived from phthalic acid, the salicylate derived from salicylic acid, the sorbate derived from sorbic acid, the stearate derived from stearic acid, the succinate derived from succinic acid, the tartrate derived from tartaric acid, the toluene-p-sulphonate derived from p-toluene sulphonic acid, and the like. Such salts may be formed by procedures well known and described in the art.

Other acids such as oxalic acid, which may not be considered pharmaceutically acceptable, may be useful in the preparation of salts useful as intermediates in obtaining a chemical compound of the invention and its pharmaceutically acceptable acid addition salt.

Metal salts of a chemical compound of the invention include alkali metal salts such as the sodium salt of a chemical compound of the invention containing a carboxy group.

Steric Isomers

The compounds of the invention may exist in (+) and (−) forms as well as in racemic forms (±). The racemates of these isomers and the individual isomers themselves are within the scope of the present invention.

Racemic forms can be resolved into the optical antipodes by known methods and techniques. One way of separating the diastereomeric salts is by use of an optically active acid, and liberating the optically active amine compound by treatment with a base. Another method for resolving racemates into the optical antipodes is based upon chromatography on an optical active matrix. Racemic compounds of the present invention can thus be resolved into their optical antipodes, e.g., by fractional crystallisation of d- or l-(tartrates, mandelates, or camphorsulphonate) salts for example.

The chemical compounds of the present invention may also be resolved by the formation of diastereomeric amides by reaction of the chemical compounds of the present invention with an optically active activated carboxylic acid such as that derived from (+) or (−) phenylalanine, (+) or (−) phenylglycine, (+) or (−) camphanic acid or by the formation of diastereomeric carbamates by reaction of the chemical compound of the present invention with an optically active chloroformate or the like.

Additional methods for the resolving the optical isomers are known in the art. Such methods include those described by Jaques J, Collet A, & Wilen S in "*Enantiomers, Racemates, and Resolutions*", John Wiley and Sons, New York (1981).

Optical active compounds can also be prepared from optical active starting materials.

Methods of Preparation

The chemical compounds of the invention may be prepared by conventional methods for chemical synthesis, e.g. those described in the working examples. The starting materials for the processes described in the present application are known or may readily be prepared by conventional methods from commercially available chemicals.

Also one compound of the invention can be converted to another compound of the invention using conventional methods.

The end products of the reactions described herein may be isolated by conventional techniques, e.g. by extraction, crystallisabon, distillation, chromatography, etc.

Biological Activity

Compounds of the invention may be tested for their ability to bind to the μ, δ, and κ opioid receptors, e.g. such as described in example 2.

Compounds that bind to opiate receptors, in particular the μ receptor, are likely to be useful in the treatment of pain, postoperative pain, chronic pain (such as cancer pain and neuropathic pain), pain during labour and delivery, drug addiction (such as heroin addiction and cocaine addiction), and alcoholism.

Furthermore, compounds that bind to opiate receptors are also likely to be useful in the treatment of irritable bowel syndrome, constipation, nausea, vomiting, and pruritic dermatoses (itching), such as allergic dermatitis and atopy. Compounds that bind to opiate receptors have also been indicated in the treatment of eating disorders, opiate overdoses, depression, smoking, sexual dysfunction, shock, stroke, spinal damage and head trauma.

Thus in further aspect, the compounds of the invention are considered useful for the treatment, prevention or alleviation of a disease, disorder or condition responsive to modulation of the opioid receptors, in particular the μ opioid receptor.

In a special embodiment, the compounds of the invention are considered useful for the treatment, prevention or alleviation of pain, postoperative pain, chronic pain, cancer pain, neuropathic pain, pain during labour and delivery, drug addiction, heroin addiction, cocaine addiction, alcoholism, irritable bowel syndrome, constipation, nausea, vomiting, pruritic dermatoses, allergic dermatitis, atopy, eating disorders, opiate overdoses, depression, smoking, sexual dysfunction, shock, stroke, spinal damage, or head trauma.

In a further embodiment, the compounds of the invention are considered particularly useful for the treatment, prevention or alleviation of pain, postoperative pain, chronic pain, drug addiction, alcoholism, and irritable bowel syndrome.

Pharmaceutical Compositions

In another aspect the invention provides novel pharmaceutical compositions comprising a therapeutically effective amount of a compound of the invention.

While a compound of the invention for use in therapy may be administered in the form of the raw chemical compound, it is preferred to introduce the active ingredient, optionally in the form of a physiologically acceptable salt, in a pharmaceutical composition together with one or more adjuvants, excipients, carriers, buffers, diluents, and/or other customary pharmaceutical auxiliaries.

In a preferred embodiment, the invention provides pharmaceutical compositions comprising a compound of the invention, or a pharmaceutically acceptable salt or derivative thereof, together with one or more pharmaceutically acceptable carriers therefore, and, optionally, other therapeutic and/or prophylactic ingredients, know and used in the art. The carrier(s) must be "acceptable" in the sense of being compatible with the other ingredients of the formulation and not harmful to the recipient thereof.

Pharmaceutical compositions of the invention may be those suitable for oral, rectal, bronchial, nasal, pulmonal, topical (including buccal and sub-lingual), transdermal, vaginal or parenteral (including cutaneous, subcutaneous, intramuscular, intraperitoneal, intravenous, intraarterial, intracerebral, intraocular injection or infusion) administration, or those in a form suitable for administration by inhalation or insufflabon, including powders and liquid aerosol administration, or by sustained release systems. Suitable examples of sustained release systems include semipermeable matrices of solid hydrophobic polymers containing the compound of the invention, which matrices may be in form of shaped articles, e.g. films or microcapsules.

The chemical compound of the invention, together with a conventional adjuvant, carrier, or diluent, may thus be placed into the form of pharmaceutical compositions and unit dosages thereof. Such forms include solids, and in particular tablets, filled capsules, powder and pellet forms, and liquids, in particular aqueous or non-aqueous solutions, suspensions, emulsions, elixirs, and capsules filled with the same, all for oral use, suppositories for rectal administration, and sterile injectable solutions for parenteral use. Such pharmaceutical compositions and unit dosage forms thereof may comprise conventional ingredients in conventional proportions, with or without additional active compounds or principles, and such unit dosage forms may contain any suitable effective amount of the active ingredient commensurate with the intended daily dosage range to be employed.

The chemical compound of the present invention can be administered in a wide variety of oral and parenteral dosage forms. It will be obvious to those skilled in the art that the following dosage forms may comprise, as the active component, either a chemical compound of the invention or a pharmaceutically acceptable salt of a chemical compound of the invention.

For preparing pharmaceutical compositions from a chemical compound of the present invention, pharmaceutically acceptable carriers can be either solid or liquid. Solid form preparations include powders, tablets, pills, capsules, cachets, suppositories, and dispersible granules. A solid carrier can be one or more substances which may also act as diluents, flavouring agents, solubilizers, lubricants, suspending agents, binders, preservatives, tablet disintegrating agents, or an encapsulating material.

In powders, the carrier is a finely divided solid, which is in a mixture with the finely divided active component.

In tablets, the active component is mixed with the carrier having the necessary binding capacity in suitable proportions and compacted in the shape and size desired.

The powders and tablets preferably contain from five or ten to about seventy percent of the active compound. Suitable carriers are magnesium carbonate, magnesium stearate, talc, sugar, lactose, pectin, dextrin, starch, gelatin, tragacanth, methylcellulose, sodium carboxymethylcellulose, a low melting wax, cocoa butter, and the like. The term "preparation" is intended to include the formulation of the active compound with encapsulating material as carrier providing a capsule in which the active component, with or without carriers, is surrounded by a carrier, which is thus in association with it. Similarly, cachets and lozenges are included. Tablets, powders, capsules, pills, cachets, and lozenges can be used as solid forms suitable for oral administration.

For preparing suppositories, a low melting wax, such as a mixture of fatty acid glyceride or cocoa butter, is first melted and the active component is dispersed homogeneously therein, as by stirring. The molten homogenous mixture is then poured into convenient sized moulds, allowed to cool, and thereby to solidify.

Compositions suitable for vaginal administration may be presented as pessaries, tampons, creams, gels, pastes, foams or sprays containing in addition to the active ingredient such carriers as are known in the art to be appropriate.

Liquid preparations include solutions, suspensions, and emulsions, for example, water or water-propylene glycol solutions. For example, parenteral injection liquid preparations can be formulated as solutions in aqueous polyethylene glycol solution.

The chemical compound according to the present invention may thus be formulated for parenteral administration (e.g. by injection, for example bolus injection or continuous infusion) and may be presented in unit dose form in ampoules, pre-filled syringes, small volume infusion or in multi-dose containers with an added preservative. The compositions may take such forms as suspensions, solutions, or emulsions in oily or aqueous vehicles, and may contain formulation agents such as suspending, stabilising and/or dispersing agents. Alternatively, the active ingredient may be in powder form, obtained by aseptic isolation of sterile solid or by lyophilization from solution, for constitution with a suitable vehicle, e.g. sterile, pyrogen-free water, before use.

Aqueous solutions suitable for oral use can be prepared by dissolving the active component in water and adding suitable colorants, flavours, stabilising and thickening agents, as desired.

Aqueous suspensions suitable for oral use can be made by dispersing the finely divided active component in water with viscous material, such as natural or synthetic gums, resins, methylcellulose, sodium carboxymethylcellulose, or other well known suspending agents.

Also included are solid form preparations, intended for conversion shortly before use to liquid form preparations for oral administration. Such liquid forms include solutions, suspensions, and emulsions. In addition to the active component such preparations may comprise colorants, flavours, stabilisers, buffers, artificial and natural sweeteners, dispersants, thickeners, solubilizing agents, and the like.

For topical administration to the epidermis the chemical compound of the invention may be formulated as ointments, creams or lotions, or as a transdermal patch. Ointments and creams may, for example, be formulated with an aqueous or oily base with the addition of suitable thickening and/or gelling agents. Lotions may be formulated with an aqueous or oily base and will in general also contain one or more emulsifying agents, stabilising agents, dispersing agents, suspending agents, thickening agents, or colouring agents.

Compositions suitable for topical administration in the mouth include lozenges comprising the active agent in a flavoured base, usually sucrose and acacia or tragacanth; pastilles comprising the active ingredient in an inert base such as gelatin and glycerine or sucrose and acacia; and mouthwashes comprising the active ingredient in a suitable liquid carrier.

Solutions or suspensions are applied directly to the nasal cavity by conventional means, for example with a dropper, pipette or spray. The compositions may be provided in single or multi-dose form.

Administration to the respiratory tract may also be achieved by means of an aerosol formulation in which the active ingredient is provided in a pressurised pack with a suitable propellant such as a chlorofluorocarbon (CFC) for example dichlorodifluoromethane, trichlorofluoromethane, or dichlorotetrafluoroethane, carbon dioxide, or other suitable gas. The aerosol may conveniently also contain a surfactant such as lecithin. The dose of drug may be controlled by provision of a metered valve.

Alternatively the active ingredients may be provided in the form of a dry powder, for example a powder mix of the compound in a suitable powder base such as lactose, starch, starch derivatives such as hydroxypropylmethyl cellulose and polyvinylpyrrolidone (PVP). Conveniently the powder carrier will form a gel in the nasal cavity. The powder composition may be presented in unit dose form for example in capsules or cartridges of, e.g., gelatin, or blister packs from which the powder may be administered by means of an inhaler.

In compositions intended for administration to the respiratory tract, including intranasal compositions, the compound will generally have a small particle size for example of the order of 5 microns or less. Such a particle size may be obtained by means known in the art, for example by micronization.

When desired, compositions adapted to give sustained release of the active ingredient may be employed.

The pharmaceutical preparations are preferably in unit dosage forms. In such form, the preparation is subdivided into unit doses containing appropriate quantities of the active component. The unit dosage form can be a packaged preparation, the package containing discrete quantities of preparation, such as packaged tablets, capsules, and powders in vials or ampoules. Also, the unit dosage form can be a capsule, tablet, cachet, or lozenge itself, or it can be the appropriate number of any of these in packaged form.

Tablets or capsules for oral administration and liquids for intravenous administration and continuous infusion are preferred compositions.

Further details on techniques for formulation and administration may be found in the latest edition of *Remington's Pharmaceutical Sciences* (Maack Publishing Co., Easton, Pa.).

A therapeutically effective dose refers to that amount of active ingredient, which ameliorates the symptoms or condition. Therapeutic efficacy and toxicity, e.g. $ED_{50}$ and $LD_{50}$, may be determined by standard pharmacological procedures in cell cultures or experimental animals. The dose ratio between therapeutic and toxic effects is the therapeutic index and may be expressed by the ratio $LD_{50}/ED_{50}$. Pharmaceutical compositions exhibiting large therapeutic indexes are preferred.

The dose administered must of course be carefully adjusted to the age, weight and condition of the individual being treated, as well as the route of administration, dosage form and regimen, and the result desired, and the exact dosage should of course be determined by the practitioner.

The actual dosage depend on the nature and severity of the disease being treated, and is within the discretion of the physician, and may be varied by titration of the dosage to the particular circumstances of this invention to produce the desired therapeutic effect. However, it is presently contemplated that pharmaceutical compositions containing of from about 0.1 to about 500 mg of active ingredient per individual dose, preferably of from about 1 to about 100 mg, most preferred of from about 1 to about 10 mg, are suitable for therapeutic treatments.

The active ingredient may be administered in one or several doses per day. A satisfactory result can, in certain instances, be obtained at a dosage as low as 0.1 µg/kg i.v. and 1 µg/kg p.o. The upper limit of the dosage range is presently considered to be about 10 mg/kg i.v. and 100 mg/kg p.o. Preferred ranges are from about 0.1 µg/kg to about 10 mg/kg/day i.v., and from about 1 µg/kg to about 100 mg/kg/day p.o.

Methods of Therapy

In another aspect the invention provides a method for the treatment, prevention or alleviation of a disease or a disorder or a condition of a living animal body, including a human, which disease, disorder or condition is responsive to modulation of the the opioid receptor, and which method comprises administering to such a living animal body, including a human, in need thereof an effective amount of a compound of the invention, or any of its enantiomers or any mixture of its enantiomers, or a pharmaceutically acceptable salt thereof.

It is at present contemplated that suitable dosage ranges are 0.1 to 1000 milligrams daily, 10-500 milligrams daily, and especially 30-100 milligrams daily, dependent as usual upon the exact mode of administration, form in which administered, the indication toward which the administration is directed, the subject involved and the body weight of the subject involved, and further the preference and experience of the physician or veterinarian in charge.

EXAMPLES

The invention is further illustrated with reference to the following examples, which are not intended to be in any way limiting to the scope of the invention as claimed.

Example 1

General: All reactions involving air sensitive reagents or intermediates were performed under nitrogen and in anhydrous solvents. Magnesium sulphate was used as drying agent in the workup-procedures and solvents were evaporated under reduced pressure.

9-Benzyl-9-azabicyclo[3.3.1]nonan-3-one and
8-benzyl-8-azabicyclo[3.2.1]nonan-3-one Were prepared according to Kashman, Y and Benary, E, J. Org. Chem., 37, 3778, (1972).

9-Benzyl-3,9-diazabicyclo-[4.2.1]-nonane and
10-benzyl-3,10-diazabicyclo-[4.3.1]-decane Were prepared according to 9-methyl-3,9-diazabicyclo-[4.2.1]-nonane [Michaels R J and Zaugg H E, J. Org. Chem., 25, 637, (1960)].

Method A (±)-1-[9-(3-Phenyl-allyl)-3,9-diaza-bicyclo[4.2.1]
non-3-yl]-propan-1-one hydrochloric acid salt
(Compound a)

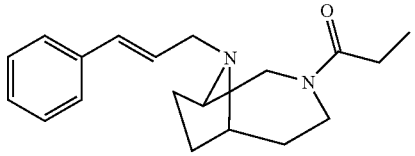

A mixture of 1-[9-H-3,9-diazabicyclo[4.2.1]non-3-yl]-propan-1-one (4.19 g, 23 mmol), potassium carbonate (3.45 g, 25 mmol), cinnamylbromide (4.73 g, 24 mmol) and acetone (100 ml) was stirred at room temperature for 15 h. The mixture was evaporated, diethylether (100 ml) was added and the mixture was washed with water (50 ml). The crude product was converted to the hydrochloric acid salt by adding a mixture of hydrochloric acid in diethyl ether (10 ml, 2.8 M). The mixture was freeze dried for 70 h. The product was isolated as amorphous material (3.9 g, 49%).

(±)-1-[10-(3-Phenyl-allyl)-3,10-diaza-bicyclo[4.3.1]
dec-3-yl]-propan-1-one fumaric acid salt (Compound b)

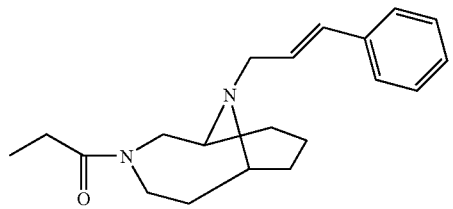

Was prepared according to method A. The whole cascade from 10-benzyl-3,10-diazabicyclo-[4.3.1]-decane was performed in the same manner as from 9-benzyl-3,9-diazabicyclo-[4.2.1]-nonane. Mp 90-94° C.

(±)-2-[9-H-3,9-diaza-bicyclo[4.2.1]non-3-yl]-propan-1-one (intermediate)

A mixture of 1-[9-benzyl-3,9-diazabicyclo[4.2.1]non-3-yl]-propan-1-one (7.4 g, 23 mmol), ethanol (100 ml, 99%), palladium on carbon (0.50 g, 10%) was stirred under hydrogen for 1 h. The mixture was filtered through celite. Yield 4.47 g (100%).

(±)-1-[9-Benzyl-3,9-diazabicyclo[4.2.1]non-3-yl]-propan-1-one

To a mixture of 9-benzyl-3,9-diazabicyclo[4.2.1]nonane (5.0 g, 23 mmol), diisopropylethylamine (4.35 ml, 25 mmol) in THF (50 ml) was added propionic acid anhydride (3.2 ml, 25 mmol) solved in THF (10 ml) over a time period of 10 min. The mixture was stirred at room-temperature for 1 h. The mixture was evaporated, aqueous sodium hydroxide (50 ml, 1M) was added and the mixture was extracted with diethyl ether (2×50 ml). The product was isolated as an oil. Yield 7.4 g (100%).

(±)-1-[3-(3-Phenyl-allyl-3,9-diazabicyclo[4.2.1]non-9-yl]-propan-1-one hydrochloric acid salt (compound c)

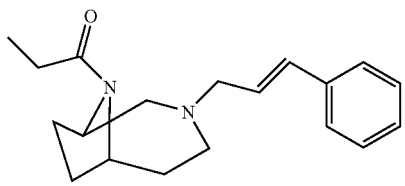

A mixture of (±)-1-[3-H-3,9-diazabicyclo[4.2.1]non-9-yl]-propan-1-one (2.25 g, 12.3 mmol), cinnamylbromide (2.56 g, 13.0 mmol), potassium carbonate (2.07 g, 15.0 mmol) and acetone (100 ml) was stirred for 3 h at 55° C. The mixture was evaporated, water (50 ml) was added and extracted with diethylether (2×50 ml). The crude product was converted to the hydrochloric acid salt by adding a mixture of hydrochloric acid in diethyl ether (5 ml, 2.8 M). The product was isolated as amorphous material (1.98 g, 48%).

(±)-1-[3-H-3,9-Diazabicyclo[4.2.1]non-9-yl]-propan-1-one

A mixture of (±)-1-[3-tert-butoxycarbonyl-3,9-diaza-bicyclo[4.2.1]non-9-yl]-propan-1-one (4.5 g, 16 mmol), trifluoroactic acid (10 ml) and dichloromethane (50 ml) was stirred for 5 h. Aqueous sodium hydroxide (50 ml) was added and the mixture was extracted with dichloromethane (3×50 ml). Yield 1.9 g (79%).

(±)-1-[3-Tert-butoxycarbonyl-3,9-diaza-bicyclo[4.2.1]non-9-yl]-propan-1-one

To a mixture of (±)-3-tert-butoxycarbonyl-3,9-diaza-bicyclo[4.2.1]nonane (4.5 g, 20 mmol), diisopropylethylamine (3.85 ml, 22 mmol) in THF (50 ml) was added propionic acid anhydride (2.82 ml, 22 mmol) solved in THF (10 ml) over a time period of 10 min. The mixture was stirred at room-temperature for 1 h. The mixture was evaporated, aqueous sodium hydroxide (50 ml, 1M) was added and the mixture was extracted with diethyl ether (2×50 ml). The product was isolated as an oil. Yield 4.7 g (84%).

(±)-9-H-3-Tert-butoxycarbonyl-3,9-diaza-bicyclo[4.2.1]nonane

A mixture of (±)-9-benzyl-3-tert-butoxycarbonyl-3,9-diaza-bicyclo[4.2.1]nonane (14.2 g, 45 mmol), ethanol (150 ml, 99%), palladium on carbon (0.5 g, 10%) was stirred under hydrogen for 1 h. The mixture was filtered through celite. Yield 10.56 g (100%).

(±)-9-Benzyl-3-tert-butoxycarbonyl-3,9-diaza-bicyclo[4.2.1]nonane

To a mixture of (±)-9-benzyl-3,9-diaza-bicyclo[4.2.1]nonane (10.35 g, 47.9 mmol) triethylamine (7.5 ml, 53 mmol) and THF, was added slowly: boc-anhydride (11.5 g, 53 mmol). The mixture was allowed to react for 30 min. The solvent was evaporated. Diethylether (100 ml) was added and the mixture was washed with water (3×50 ml). Yield 14.5 g (96%).

Example 2

Binding Data

The compounds have been tested in binding assays using human recombinant opiate δ-, κ- and μ receptors. The assays were conducted as previously described by Simonin F et al [Simonin F et al, Mol. Pharmacol., 46(6), 1015-21, 1994], Simonin F et al [Simonin F et al, Proc. Natl. Acad. Sci. USA, 92(15), 7006-10, 1995], and Wang J B et al [Wang J B et al, FEBS Lett., 348(1), 75-9, 1994], The test results are presented in Table 1 below.

TABLE 1

| Compound | δ | κ | μ |
|---|---|---|---|
|  | | $K_i$ (μM) | |
| a | 51% inhib at 10 μM | 78% inhib at 10 μM | 0.02 |
| b | 35% inhib at 10 μM | 74% inhib at 10 μM | 63% inhib at 100 nM |
| c | 34% inhib at 10 μM | 22% inhib at 10 μM | 0.022 |

Furthermore, one compound, compound b, was tested for functional activity in guinea pig ileum. The assay was conducted as previously described by Maguire P et al [Maguire P et al, Eur. J. Pharmacol., 213(2), 219-25, 1992].

Compound b was determined to be a full agonist with an $EC_{50}$ of 0.068 μM.

The invention claimed is:

1. A compound formula (I),

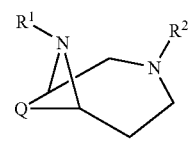

any of its enantiomers or any mixture of its enantiomers, or a pharmaceutically acceptable salt thereof, wherein Q is —$CH_2$—$CH_2$— or —$CH_2$—$CH_2$—$CH_2$—; one of $R^1$ and $R^2$ is —$CH_2$—$CH_2$—$CH_2$—$R^3$, —$CH_2$—CH═CH—$R^3$, or —$CH_2$—C≡C—$R^3$; wherein $R^3$ is aryl or heteroaryl; which aryl and heteroaryl is optionally substituted with one or more substituents selected from the group consisting of: halogen, hydroxy, amino, cyano, nitro, trifluoromethyl, alkoxy, cycloalkoxy, alkyl, cycloalkyl, cycloalkylalkyl, alkenyl, and alkynyl; and the other of $R^1$ and $R^2$ is —CO—$R^4$; wherein $R^4$ is alkyl, cycloalkyl, cycloalkylalkyl, aryl, or arylalkyl.

2. The compound according to claim 1 or any of its enantiomers or any mixture of its enantiomers, or a pharmaceutically acceptable salt thereof, wherein Q is —$CH_2$—$CH_2$—.

3. The compound according to claim 1 or any of its enantiomers or any mixture of its enantiomers, or a pharmaceutically acceptable salt thereof, wherein Q is —$CH_2$—$CH_2$—$CH_2$—.

4. The compound according to claim 1 or any of its enantiomers or any mixture of its enantiomers, or a pharmaceutically acceptable salt thereof, wherein one of $R^1$ and $R^2$ is —$CH_2$—CH=CH—$R^3$; wherein $R^3$ is defined as in claim 1.

5. The compound according to claim 1 or any of its enantiomers or any mixture of its enantiomers, or a pharmaceutically acceptable salt thereof, wherein $R^4$ is alkyl.

6. The compound according to claim 1 or any of its enantiomers or any mixture of its enantiomers, or a pharmaceutically acceptable salt thereof, wherein Q is —$CH_2$—$CH_2$— or —$CH_2$—$CH_2$—$CH_2$—; one of $R^1$ and $R^2$ is —$CH_2$—CH=CH—$R^3$, or —$CH_2$—C≡C—$R^3$; wherein $R^3$ is phenyl; and the other of $R^1$ and $R^2$ is —CO—$R^4$; wherein $R^4$ is alkyl.

7. A compound of claim 1, which is (±)-1-[9-(3-Phenyl-allyl)-3,9 diaza-bicyclo[4.2.1]non-3-yl]-propan-1-one; (±)-1-[10-(3-Phenyl-allyl)-3,10-diaza bicyclo[4.3.1]dec-3-yl]-propan-1-one; (±)-1-[3-(3-Phenyl-allyl)-3,9-diazabicyclo[4.2.1]non-9-yl]-propan-1-one; or any of its enantiomers or any mixture of its enantiomers, or a pharmaceutically acceptable salt thereof.

8. A pharmaceutical composition, comprising a therapeutically effective amount of a compound of claim 1, or any of its enantiomers or any mixture of its enantiomers, or a pharmaceutically acceptable salt thereof, together with at least one pharmaceutically acceptable carrier, excipient or diluent.

9. A method for treatment or alleviation of a disease or a disorder or a condition of a living animal body, including a human, which disorder, disease or condition is responsive to modulation of the opioid receptor, which method comprises the step of administering to such a living animal body in need thereof a therapeutically effective amount of a compound according to claim 1, or any of its enantiomers or any mixture of its enantiomers, or a pharmaceutically acceptable salt thereof; wherein the disease, disorder or condition responsive to modulation of the opioid receptor is pain.

10. The method according to claim 9, wherein said pain is postoperative pain, chronic pain, cancer pain, neuropathic pain or pain during labor and delivery.

* * * * *